Figure 1:
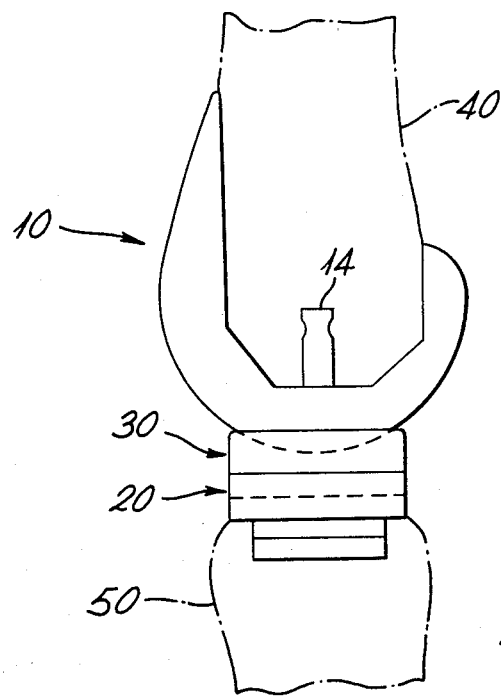

United States Patent [19]

Polyzoides et al.

[11] 4,353,136
[45] Oct. 12, 1982

[54] ENDOPROSTHETIC KNEE JOINT

[76] Inventors: Apostolos J. Polyzoides, Breakway, School Rd., Hockley Heath, Lapworth, West Midlands, England; Athanassios Tsakonas, 5 Agiou Serafim St., Salonika 366, Greece

[21] Appl. No.: 204,269

[22] Filed: Nov. 5, 1980

[51] Int. Cl.$^3$ .............................................. A61F 1/24
[52] U.S. Cl. .................................. 3/1.911; 128/92 C
[58] Field of Search ............................. 3/1.911, 1.91; 128/92 C

[56] References Cited

U.S. PATENT DOCUMENTS

| | | | |
|---|---|---|---|
| 3,816,855 | 6/1974 | Saleh | 3/1.911 |
| 4,085,466 | 4/1978 | Goodfellow et al. | 3/1.911 X |
| 4,216,549 | 8/1980 | Hillberry et al. | 3/1.911 |
| 4,219,893 | 9/1980 | Noiles | 3/1.911 |

FOREIGN PATENT DOCUMENTS

| | | | |
|---|---|---|---|
| 1507309 | 4/1978 | United Kingdom | 3/1.911 |
| 1509366 | 5/1978 | United Kingdom | 3/1.911 |
| 1534263 | 11/1978 | United Kingdom | 3/1.911 |
| 1553836 | 10/1979 | United Kingdom | 3/1.911 |
| 1567007 | 5/1980 | United Kingdom | 3/1.911 |

Primary Examiner—Ronald L. Frinks
Attorney, Agent, or Firm—Cushman, Darby & Cushman

[57] ABSTRACT

Endoprosthetic knee joint devices are described in British Patent No. 1,534,263 comprising an associated pair of femoral and tibial components respectively having convex and relatively flattened articulatory bearing surfaces, and an intervening meniscal component having opposed articulatory bearing surfaces respectively substantially complementary with said femoral and tibial surfaces. It is now proposed that such devices be improved in stability by the provision of mutually slidably engageable rib and groove formations of longitudinally curved form, one each in the complementary tibial and meniscal surfaces, the groove preferably being located in the meniscal component.

5 Claims, 8 Drawing Figures

ENDOPROSTHETIC KNEE JOINT

This invention concerns endoprosthetic bone joint devices and more particularly such devices for the knee joint.

In British Patent Specification No. 1,534,263 (corresponding approximately to U.S. Pat. No. 4,085,466) there is described an endoprosthetic knee joint device comprising a femoral condylar component for securement to the femur and having a convexly curved articulatory bearing surface, a tibial condylar component for securement to the tibia and having a relatively flattened articulatory bearing surface compared to that of said femoral component, and a meniscal component having two articulatory bearing surfaces in opposed disposition and of individual forms respectively substantially complementary to said femoral and tibial component articulatory surfaces, the various surface engagements being non-captive. Such a device is referred to hereinafter as being of the kind defined hereinbefore.

This previously proposed device affords the advantage of resolving contradictory requirements facing prior art devices which did not involve any separate meniscal component, these requirements being the matching of the condylar articulatory bearing surfaces to attain uniform load distrubution therebetween when directly engaged, and the provision of multiple freedoms of movement to allow close simulation of the mutual articulatory movements in the natural joint. However, in its simpler forms the device of said Specification is open to a possible objection that meniscal component retention between the femoral and tibial components is not secure. Indeed, said Specification describes a further form of device in which the meniscal component is linked with the tibial component to obviate this objection, but such further form can be viewed as complicated for the purposes of manufacture.

An object of the present invention is to improve this situation by enhancing the meniscal component stability without unduly complicating the device and restricting the articulatory function.

According to the present invention there is provided a device of the kind defined hereinbefore in which one of the articulatory surfaces of said meniscal and tibial components is formed with a longitudinally arcuate groove therein and the other of said surfaces is formed with a rib projecting therefrom for slidable engagement in said groove.

In the presently proposed device the groove and rib are preferably of longitudinally circular arcuate, substantially complementary forms. Also, the groove is conveniently located in the tibial component where a greater body of material can be made available for this purpose.

It is also preferred at present that the invention is of a so-called bicondylar form in which the tibial and femoral components each have separate articulatory bearing portions joined in a side-by-side spaced disposition for respective location in the lateral and medial compartments of the knee.

In a first such bicondylar form the bearing portions of each of the femoral and tibial components are joined by an anteriorly located portion, the tibial component has a single common groove or rib extending successively across each of the bearing and joining portions thereof, and two separate meniscal components are provided for respective location in the lateral and medial compartments. This form is suited to a knee subject to a less severe condition in which cruciate ligament function remains, these ligaments being accommodated during surgery in the gap between the bearing portions and behind the joining portion of the femoral component, in the similar gap in the tibial component, and the intervening gap between the meniscal components.

In a second bicondylar form, modified relative to that just described, the meniscal components are also joined. This modified form is suited to a more severely disabled knee in which the cruciate ligament function cannot be salvaged and it is, of course, unnecessary for the components to have gaps to accommodate these ligaments. Also, in this case it is preferred that the integrated meniscal component have a peg or other upstanding portion which co-operates with a groove extending between the bearing portion of the femoral component in order to provide enhanced lateral stability of the device.

Figure 2:
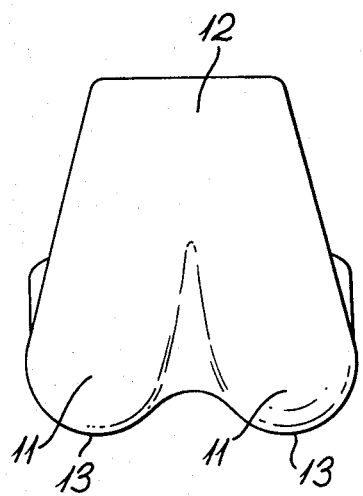
Figure 3:
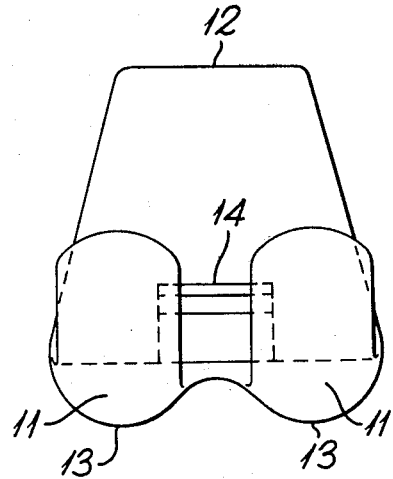
Figure 4:
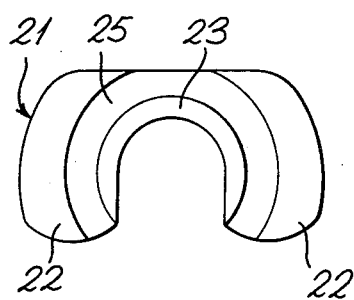
Figure 6:
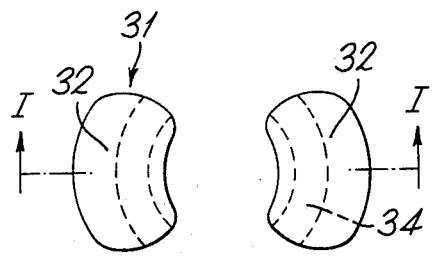
Figure 5:
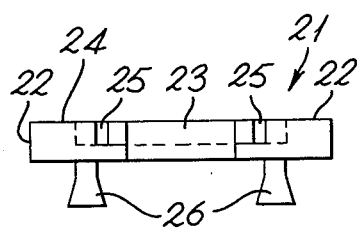
Figure 7:
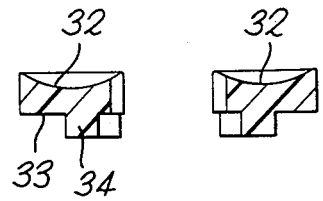
Figure 8:
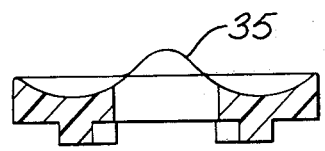

In order that the present invention and its benefits may be more fully and clearly understood, the invention will now be described by way of example with reference to the accompanying drawings, in which:

FIG. 1 illustrates in side view a presently preferred embodiment of the invention, this being of the above-mentioned first bicondylar form;

FIGS. 2 and 3 further illustrate the femoral component of FIG. 1 respectively in front and rear views;

FIGS. 4 and 5 further illustrate the tibial component of FIG. 1 respectively in plan and front views;

FIGS. 6 and 7 further illustrate the meniscal components of FIG. 1 respectively in plan view and a sectional view taken on I—I in FIG. 6; and FIG. 8 illustrates in a sectional view corresponding to that of FIG. 7 a modified, integrated meniscal component for use in another embodiment of the invention of the above-mentioned second bicondylar form.

The device of FIG. 1 comprises a femoral component 10, a tibial component 20, and a pair of meniscal components 30 of which only one is seen in the relevant side view.

The femoral component is of a general form which is already known and comprises, as further shown by FIGS. 2 and 3, a pair of like elongated articulatory bearing portions 11 joined at corresponding end regions in side-by-side spaced disposition by a web portion 12. The bearing portions 11 are each curved longitudinally and transversely to define convex bearing surfaces 13 which are substantially part-spheroidally shaped, and the web portion 12 defines a grooved region therebetween. The component 10 is adapted for securement to the distal end of the femur, denoted in broken line at 40 in FIG. 1, with the bearing portions 11 respectively located to replace the condylar surface regions, and with the web portion 12 located anteriorly for co-operation with the patella. In the present case this securement will involve the use of so-called bone cement, and the adaptation involves the provision of a tonque 14 upstanding from the concave surface of the component 10.

The tibial component 20 is seen from the further illustration of FIGS. 4 and 5 to comprise a C-shaped platform 21, the end part of which serve as articulatory bearing portions 22 joined in spaced side-by-side disposition by the intermediate part as a link portion 23. The major surfaces of the platform are planar and parallel, but with one such surface 24 having a C-shaped circular arcuate groove 25 therein, and the other surface having two ribs 26 of dovetail sectional form extending thereacross. The groove 25 extends across each portion of the platform, with the ends of the groove opening into the side surfaces of the bearing portions 22 and the central part of the groove opening at one side therof into the convex side surface of link portion 23. The ribs 26 are longitudinally rectilinear and extend in mutually parallel manner across respective ones of the bearing portions 22.

The component 20 is adapted for securement to the proximal end of the tibia, denoted in broken outline at 50 in FIG. 1, with the bearing portions 22 respectively located to replace the condylar surface regions, and with the link portion 23 located anteriorly in place of the intracondylar notch. Again, this securement will involve the use of bone cement, and in this case the adaptation involves the ribs 26.

Turning now to the meniscal components 30, these are both shown in FIGS. 6 and 7 from which it will be seen that they are of like form. Each component 30 comprises a platform 31 of elongate arcuate shape as seen in plan view, this shape being similar to, and no greater than, one free end part of the C-shaped tibial component platform. The platform 31 has one major surface 32 dished to a substantially part-spheroidally concave shape complementary to that of the femoral component surfaces 13, and the opposed major surface 33 is planar. A rib 34 projects from the surface 33, this rib being circularly arcuate along its length and following the arcuate shape of the platform 31. The rib 34 is complementary with the tibial component groove 25 for longitudinal sliding engagement therewith.

The use of the illustrated device is generally indicated by FIG. 1: the femoral and tibial components are suitably secured to their respective bones as briefly discussed above, and the meniscal components are located therebetween with the surfaces 32 and 33 of the former respectively engaged with the surfaces 13 and 24 of the latter. It is to be noted that this location also involves inter-engagement of the meniscal component ribs 34 with the tibial component groove 24. It is also to be noted that the various inter-component engagements are non-captive.

The overall result is a bicondylar assembly allowing retention of the cruciate ligaments; a flexible choice of materials to afford compound advantages, such as metal femoral and tibial components for stable securement and plastics material meniscal components for low friction articulation with the metal components; and, if appropriate at some later stage, replacement of the meniscal components without the need for separation of bone/prosthesis securements.

Functionally, the device allows flexion-extension movement by articulation between the femoral and meniscal component surfaces 13 amd 32, and rotation about the longitudinal axis of the leg by articulation between the tibial and meniscal component surfaces 24 and 33 together with sliding between the groove 25 and ribs 34 of these components. The last-mentioned groove and ribs also serve by their inter-engagement to stabilize the meniscal components against dislocation.

While the invention has been described more particularly with reference to the illustrated embodiment, it can clearly be subjected to variation within the broader expression of the invention in the foregoing introductory discussion. For example the meniscal components can be integrated in similar manner to the bearing portions of the femoral and tibial components to provide a second bicondylar form as mentioned above, and FIG. 8 illustrates an integrated meniscal component co-operable with the illustrated femoral and tibial components for this purpose, although it may be preferred that no component have a gap or slot therein. Also, it will be noted in FIG. 8 that the meniscal component has an upstanding portion 35 which co-operates with the groove between the bearing portions of the femoral component. Conversely to this variation, the femoral and/or tibial components can be provided in wholly separated bicondylar form similarly to the meniscal components of FIGS. 6 and 7.

We claim:

1. An endoprosthetic knee joint device of bicondylar form comprising a femoral component for securement to the femur and having two separate articulatory bearing portions joined together at least at their anterior regions in a side-by-side spaced disposition for respective location in the lateral and medial compartments of the knee, a tibial component for securement to the tibia and having two separate articulatory bearing portions joined together at least at their anterior regions in a side-by-side spaced disposition for respective location in said compartments, and a meniscal component having two separate articulatory bearing portions for respective location in said compartments between said femoral and tibial component portions, each said femoral component portion having a convexly curved articulatory bearing surface portion, each said tibial component portion having a relatively flattened articulatory bearing surface portion, each said meniscal component portion having two articulatory bearing surface portions in opposed disposition and of individual forms substantially complementary to and engaged with the said tibial component having one of a longitudinally arcuate groove and a rib extending in a singular form extending across both of the bearing and joining portions thereof, said meniscal component portions each having a portion of the other of said groove and rib slidably engaged in said one thereof, and each of said engagements being non-captive.

2. A device according to claim 1 wherein said groove and rib are of longitudinally circular arcuate, substantially complementary forms.

3. A device according to claim 1 or 2 wherein said groove is located in said tibial component.

4. A device according to claim 1 wherein said meniscal component portions are wholly separate and of like form interchangeable between said compartments.

5. A device according to claim 1 wherein said two meniscal component portions are also joined together at least at their anterior regions, and the joining portion therebetween is at least partly upstanding relative to the articulatory surface complementary with that of said femoral component.

* * * * *